(12) United States Patent
Wagenaar Cacciola et al.

(10) Patent No.: US 10,507,336 B2
(45) Date of Patent: Dec. 17, 2019

(54) LIGHT TREATMENT SYSTEM

(71) Applicant: KONINKLIJKE PHILIPS N.V., Eindhoven (NL)

(72) Inventors: Giovanna Wagenaar Cacciola, Eindhoven (NL); Georges Marie Calon, Eindhoven (NL); Ian Edward Ashdown, West Vancouver (CA); Damien Gerard Loveland, Richmond (CA); Adriaantje Pieternella Mouws-Van Rossum, Wintelre (NL); Claudia Mutter, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 68 days.

(21) Appl. No.: 15/212,622

(22) Filed: Jul. 18, 2016

(65) Prior Publication Data

US 2016/0325114 A1 Nov. 10, 2016

Related U.S. Application Data

(63) Continuation of application No. 13/381,385, filed as application No. PCT/IB2010/052895 on Jun. 24, 2010, now Pat. No. 9,415,237.

(30) Foreign Application Priority Data

Jun. 30, 2009 (EP) .................................... 09164173

(51) Int. Cl.
*A61N 5/06* (2006.01)
*A61N 5/067* (2006.01)

(52) U.S. Cl.
CPC .......... *A61N 5/0616* (2013.01); *A61N 5/062* (2013.01); *A61N 2005/067* (2013.01); *A61N 2005/0645* (2013.01); *A61N 2005/0651* (2013.01); *A61N 2005/0653* (2013.01); *A61N 2005/0659* (2013.01); *A61N 2005/0661* (2013.01); *A61N 2005/0662* (2013.01)

(58) Field of Classification Search
USPC ............. 606/2–19; 607/86–94; 128/898–900
See application file for complete search history.

(56) References Cited

U.S. PATENT DOCUMENTS

| 5,800,479 | A | 9/1998 | Thiberg |
| 5,824,023 | A * | 10/1998 | Anderson ............ A61B 18/203 |
| | | | 607/88 |
| 6,663,659 | B2 | 12/2003 | McDaniel |
| 7,255,458 | B2 | 8/2007 | Ashdown |
| 7,311,722 | B2 | 12/2007 | Larsen |
| 2003/0114902 | A1 | 6/2003 | Prescott |
| 2005/0251242 | A1 * | 11/2005 | Bousfield ............... A61N 1/322 |
| | | | 607/150 |

(Continued)

*Primary Examiner* — Carl H Layno
*Assistant Examiner* — Dacheng Xie

(57) ABSTRACT

The invention relates to a light treatment system. The light treatment system comprises a light source for emitting light for illuminating a part of a human or animal body for light treatment. The light treatment system further comprises a housing for emitting light towards the part of the human or animal body, and for at least partially covering the illuminated part of the human or animal body from view. The housing further comprises a window for emitting light from an inner part of the housing away from the housing.

18 Claims, 3 Drawing Sheets

(56) References Cited

U.S. PATENT DOCUMENTS

| | | | |
|---|---|---|---|
| 2006/0030909 A1* | 2/2006 | Karni | A61B 18/203 607/94 |
| 2006/0217787 A1 | 9/2006 | Olson et al. | |
| 2006/0247742 A1 | 11/2006 | Lee | |
| 2007/0198004 A1* | 8/2007 | Altshuler | A61B 18/203 606/9 |

* cited by examiner

LIGHT TREATMENT SYSTEM

CROSS-REFERENCE TO PRIOR APPLICATIONS

This application claims the benefit of priority of and describes relationships between the following applications: wherein this application is a continuation of U.S. patent application Ser. No. 13/381,385, filed Mar. 16, 2012, issued as U.S. Pat. No. 9,415,237, which is a National Stage of International Application No. PCT/IB2010/052895, filed Jun. 24, 2010, which claims the priority of foreign application EP09164173.8 filed Jun. 30, 2009, all of which are incorporated herein in whole by reference.

FIELD OF THE INVENTION

The invention relates to a light treatment system.

BACKGROUND OF THE INVENTION

Light treatment systems are known per se. They are used, inter alia, in skin treatment systems for providing skin treatment for cosmetic and medical applications. Medical light treatment, for example, comprises light treatment using ultraviolet light radiation for treatment of, for example, psoriasis and, for example, red or blue light treatment, combined with a photosensitizer, for the treatment of, for example, skin-cancer. Cosmetic light treatments, for example, comprise skin rejuvenation using, for example, a mixture of infrared light and amber light. Such a skin rejuvenation process is, for example, described in the U.S. Pat. No. 6,663,659.

Another system for skin treatment through illumination of light is known from WO 2008/058713. In this skin treatment device for irradiating a skin area, the skin treatment device has an elastic at least partially hollow ring structure for leak-proof placement of the skin treatment device onto the skin. In another embodiment the skin treatment device, has a handle portion including a radiation source capable of emitting the electromagnetic radiation and a detachably mounted attachment having the elastic at least partially hollow ring structure for the leak-proof placement of the skin treatment device onto the skin.

A trend in such known light treatment devices is that they are designed to be battery operated such that an operator of the light treatment device may freely use the light treatment device without being limited in its use by a wire providing power or light to the light treatment device. For battery operated equipment, the power required by the equipment is typically always too high.

SUMMARY OF THE INVENTION

So it is an object of the invention to provide a light treatment device which has reduced power usage.

According to a first aspect of the invention the object is achieved with a light treatment system as claimed in claim 1.

The light treatment system according to the first aspect of the invention comprises a light source for emitting light for illuminating a part of a human or animal body for light treatment, the light treatment system comprising a housing for emitting light towards the part of the human or animal body, and for at least partially covering the illuminated part of the human or animal body from view, the housing comprising a window for emitting light from an inner part of the housing away from the housing.

A rim between the housing and the human or animal body via which light may leak away from the housing is not considered to be a window for allowing light from the inner part of the housing to be emitted away from the housing, because such a rim between the housing and the human or animal body is not part of the housing. Such uncontrolled leakage of light is usually undesirable and is preferably to be avoided as the intensity of the leaked light is difficult to control which might be dangerous to people working with the light treatment system and which may be annoying for people working with the light treatment system. Furthermore, the wavelength of the light for illuminating the part of the human or animal body may be harmful to humans and as such leakage of light from the rim between the human or animal body and the housing of the light treatment system is to be avoided.

Light emitted by the light source for light treatment may comprise light visible to the naked human eye and/or may comprise light invisible to the naked human eye, such as infrared light and/or ultraviolet light. The light source may also be configured for emitting light having a relatively broad emission spectrum which may comprise a substantially continuous spectrum over a predefined range or which may comprise a discontinuous spectrum over the predefined range. Such a discontinuous spectrum may comprise a plurality of emission peaks of individual light emitters inside the light source. Such individual light emitters may, for example, emit light around a central wavelength having a relatively narrow spectral peak. Light emitters emitting a relatively narrow spectral peak, for example, comprise semiconductor light emitters such as light emitting diodes, laser diode and/or organic light emitting diodes. Light emitters emitting a relatively broad and substantially continuous spectrum may comprise all types of lamps emitting a relatively broad spectrum. The emission spectrum of a light emitter may, for example, be enhanced via the use of luminescent materials.

An effect of the light treatment system according to the invention is that the window in the housing may be used as indicator whether the light treatment system is operating and/or functioning well. The use of the window as indicator for the operation or functioning of the light treatment system has a benefit in that no additional light source and/or electronic circuitry is required for indicating whether the light treatment system is operating. Especially when using battery-operated light treatment systems, the power requirements of the light treatment system as a whole determine the operational time between battery-charges during which the light treatment system may operate. An additional light source and/or electronic circuitry would then reduce the operational time between battery-charges which would not be preferred.

A further benefit of the light treatment system according to the invention is that it is more cost effective, because the additional cost of the additional light source and/or electronic circuitry is not required. As the light treatment system may be a consumer system which consumers may use, for example, at home for light treatment, the cost of the light treatment system is an important competitive advantage. Furthermore, the high number of light treatment systems which may be required for a consumer market may make an even marginal cost reduction beneficial to the producer of the light treatment system.

In an embodiment of the light treatments system, the light emitted via the window comprises light of a different wavelength compared to the light emitted by the light treatments system towards the part of the human or animal body. This may, for example, result from light conversion means being present inside the housing to convert at least a part of the light emitted towards the human or animal body into light of a different wavelength.

So, in an embodiment of the light treatments system, light conversion means are present inside the housing, the light conversion means being configured for converting light impinging on the conversion means into light of a longer wavelength. The light conversion means may be part of the light treatment in which, for example, an ointment, salve or cream may be applied to the part of the human or animal body, for example, to improve the absorption of the light emitted by the light treatment system and/or to generate a light-enhanced or light-initiated chemical reaction which is required or beneficial for the light treatment therapy. In such ointment, salve or cream, the light conversion means may be present or added to convert a part of the light emitted by the light treatment system and impinging on the ointment, salve or cream to be converted into light having the different wavelength. Alternatively, the light conversion means may be applied to a wall of the housing of the light treatment system.

In an embodiment of the light treatments system, the window comprises the light conversion means for converting light impinging on the luminescent material into light of a longer wavelength. When using the window in the housing as indicator to provide information about the working of the light treatment system, such indicator often is required to emit light of a specific color, for example, the color red. Skin treatment may be done using light of a completely different color, for example, using substantially blue light or even radiation not visible to the human eye. A simple filtering of the light to only transmit the required component of the light may not work because the light used for the treatment may not comprise the required color component. In such a situation, a thin layer of luminescent material on the window or implemented inside the window may be sufficient to convert light used for the light treatment on the part of the human or animal body into light of a longer wavelength, for example, into red light. As such, a red indicator window is generated which emits red light when the light treatment system is in operation by converting at least a part of the light which is emitted towards the part of the human or animal body and which impinges on the window, into light of the longer wavelength, for example, light of the color red. Of course any color may be used to provide the user with information about the working of the light treatment system.

In an embodiment of the light treatments system, the light conversion means are configured for absorbing ultraviolet light and for converting a part of the absorbed ultraviolet light into visible light. Especially when using light which is invisible to the naked human eye, a simple window in the housing will not be sufficient to indicate that the light treatment system is working properly. Luminescent material as indicated in the previous part may be required. For some skin treatments, ultraviolet light is used, and for others infrared light is used. Such ultraviolet or infrared light may be harmful to the human eye and as such the housing of the light treatment system may be used to shield the harmful light from the human eye. Still, there should be a low-cost way to provide the user with information whether or not the light treatment system is working properly. An indicator light may be used which however adds to the cost of the light treatment system or which may reduce the operational lifetime between battery-charges of a battery-operated system, as indicated previously. Typically a part of the light emitted by the light treatment system toward the part of the human or animal body will reflect from the human or animal body back into the housing. This reflected light may be indicated as stray light and only marginally contributes to the treatment effect. Some of this reflected light may, for example, impinge on the window comprising the luminescent material and the luminescent material of the window may convert some of the impinging ultraviolet light into visible light used to indicate the operation of the light treatment system.

A further benefit of this conversion of the ultraviolet light into visible light is that the operation and/or functioning of the light treatment system can be inspected relatively safely, as the luminescent material converts the part of the ultraviolet light into visible light which is safe to the human or animal eye. In addition, the window through which the converted light is visible from outside the housing does not need to be manufactured of specific material to transmit ultraviolet radiation. In a preferred embodiment of the light treatment system the luminescent material is applied to a wall of the window facing toward the part of the human or animal body, or said differently, facing the inner part of the housing. In such an arrangement, the ultraviolet light is converted into visible light before the light transits the window in the light treatment system. Because materials which are transmissive for ultraviolet typically are relatively expensive, the use of the luminescent material for converting ultraviolet light into visible light omits the need for the ultraviolet transmissive materials and as such reduces the cost of the light treatment system.

In an embodiment of the light treatments system, the light treatment system comprises a control circuit being configured for controlling the light source for emitting the light towards the part of the human or animal body in a pulsed mode operation comprising a dead-time during which no light is emitted by the light treatment system towards the part of the human or animal body. For most light treatment sequences, a pulsed mode of operation of the light emitted toward the part of the human or animal body is required. As different treatment sequences may require a different frequency and/or a different dead-time, the light treatment system according to the invention comprises the control circuit.

In an embodiment of the light treatments system, the control circuit is configured for controlling a frequency and/or dead-time of the pulsed mode operation, the frequency and/or dead-time being selected for being perceived by a naked human eye as a substantially continuous illumination of the part of the human or animal body while still providing an effective light treatment. Using, for example, a frequency above, for example, 50 Hertz, the flashing of the light source is perceived as a substantial continuous light source by the human eye. Flashing light sources may be perceived relatively annoying. Especially when having to work with such flashing light sources for a considerable time the flashing light may even cause health problems to the people using them, such as headache or dizziness or even epileptic attacks. For light treatment systems the dead-time may be more important to obtain an effective light treatment compared to the overall frequency of the pulsed mode operation. As such, the control circuit may be configured to control the frequency and/or dead-time of the pulsed mode operation such that the light emitted by the window is perceived by the human eye as continuous light while still providing an effective light treatment. As such, working conditions for people operating the light treatment system may be improved substantially and problems such as headache, dizziness or epileptic attacks may be avoided.

In an embodiment of the light treatments system, the window comprises a further light source controlled by the control circuit for emitting light during at least a part of the dead-time during which no light is emitted by the light treatment system towards the part of the human or animal body. Such use of the further light source may provide similar beneficial effects in relation to the working conditions for the people operating the light treatment systems as mentioned above. Because the further light source is switched on during at least a part of the dead-time during which no light is emitted by the light treatment system towards the part of the human or animal body, this additional light from the further light source may cause the light emitted from the window to be perceived as a substantial continuous emission of light, thus reducing any negative effects resulting from flashing lights, thus improving the working conditions of the people operating the light treatment systems.

In an embodiment of the light treatments system, the light treatment system comprises the light conversion means comprising luminescent material, wherein the luminescent material comprises a decay time being configured for reducing the dead-time of the light treatment system for generating a light emission from the window being perceived by the naked human eye as a continuous light emission. The decay time of the luminescent material may, for example, be longer than the dead-time to generate a substantial continuous emission of light from the window. Alternatively, the decay time may be chosen such that the remaining dead-time is too short to be noticed by the naked human eye such that the emission from the window is perceived as being continuous by the naked human eye. The use of the luminescent material having a decay time configured for reducing the dead-time to generate a perceived continuous light emission results in a further alternative manner to cause the light emitted by the window to be perceived as continuous light emitted from the window of the light treatment system. When the decay time is longer than the dead-time, the luminescent material will continue to emit light while the light source of the light treatment system is not emitting light towards the part of the human or animal body. There may be some residual intensity variations visible via the window.

In an embodiment of the light treatments system, the housing comprises resilient material for contacting the human or animal body. Contact between the human or animal body and the housing via the resilient material is typically more pleasant to the humans or animals having to undergo the light treatment.

In an embodiment of the light treatments system, the resilient material is configured for contacting the human or animal body for preventing light to leak away from the housing. Especially when using ultraviolet light for the light treatment, the leakage of ultraviolet light should be avoided, both to protect the eyes of the person operating the light treatment system and to reduce the exposure to ultraviolet light to the person operating the light treatment system and to the remainder of the human or animal body which does not require the treatment. When, for example, the light treatment system is used for the treatment of psoriasis or vitiligo, relatively harmful ultraviolet radiation is used. This radiation may be harmful to the remainder of the body and exposure to that specific ultraviolet light should be avoided. Using the resilient material according to the current embodiment ensures that the possible harmful ultraviolet radiation does not leak away from the housing.

In an embodiment of the light treatments system, the window is arranged in the resilient material. The intensity of the stray light near the part of the human or animal body which is to be illuminated is relatively high, thus allowing good visibility of the stray light emitted via the window in the resilient material. Furthermore, as the window is arranged in the resilient material, part of the window may also be resilient allowing a user to manipulate the dimensions of the window by manipulating the amount of force with which the light treatment system is applied to the human or animal body. If, for example, the intensity of the light emitted from the window is relatively high, the dimensions of the window may be reduced by increasing the force with which the light treatment system is applied, thus reducing the intensity of the light emitted from the window.

In an embodiment of the light treatments system, the light source comprises a first light emitter and a second light emitter, the first light emitter emitting light comprising a different spectrum compared to the second light emitter. Typically light comprising a mixture of different wavelengths is required to obtain an effective light treatment. Well known mixtures for, for example, skin rejuvenation is by mixing infra-red light with amber light which is emitted toward the part of the human or animal body at a predefined frequency and/or dead-time. Instead of applying a single light source which emits a spectrum comprising the required wavelength peaks in its spectrum, the light source preferably comprises a plurality of light emitters in which each of the light emitters contributes part of the spectrum of the light required for the treatment. Especially the use of light emitting diodes or other solid-state light emitters such as laser diodes, organic light emitting diode may beneficially be used, to generate the required spectrum of light for the light treatment may be preferred as such solid-state light emitters typically have a relatively high efficiency and as such may be very beneficial when the light treatment system is battery-operated.

In an embodiment of the light treatments system, the control circuit for controlling the light source for emitting the light towards the part of the human or animal body in a pulsed mode operation, wherein the control circuit is configured for controlling the first light emitter to emit light at a first pulsed mode of operation and for controlling the second light emitter to emit light at a second pulsed mode of operation being different from the first pulsed mode of operation. Such a control circuit may allow the spectrum of the light applied via the light treatment system to vary in time which allows maximum flexibility in applying the light treatment.

In an embodiment of the light treatments system, the first light emitter emits ultraviolet light and the second light emitter emits visible light. The combination of ultraviolet light and visible light may be beneficial for, for example, preparing the skin to the ultraviolet light treatment, or, for example, for relieving the skin with visible light after a treatment with ultraviolet light.

In an embodiment of the light treatments system, the first light emitter emits ultraviolet light and the second light emitter emits infrared light. The combination of ultraviolet light and infrared light may be beneficial for locally increasing the temperature to, for example, improve the blood flow, and for relieving the pain before, during or after the treatment with ultraviolet light.

In an embodiment of the light treatments system, the first light emitter emits visible light and the second light emitter emits infrared light. The combination of visible light and infrared light may be beneficial for locally increasing the temperature and improve blood flow.

In an embodiment of the light treatments system, the first light emitter emits ultraviolet light comprising light of a first wavelength and the second light emitter emits ultraviolet light comprising light of a second wavelength. The combination of ultraviolet light comprising light of the first wavelength and the second wavelength may be beneficial when a broader range of ultraviolet light is needed than a single light emitter may be able to provide.

In an embodiment of the light treatments system, the first light emitter emits visible light and the second light emitter emits visible light. Especially in the treatment of skin-cancer different photosensitizers may be used which require different wavelengths of visible light.

In an embodiment of the light treatments system, the light treatment system comprises massage means for massaging the part of the human or animal body. A benefit of the adding of massage means is that the blood circulation at the part of the human or animal body is improved which further improves the effectiveness of the light treatment. A further benefit is that the massage means may provide relaxation to the human or animal body making the light treatment more pleasant to the human or animal undergoing the treatment.

In an embodiment of the light treatments system, the light treatment system comprises dispensing means for dispensing a substance to the part of the human or animal body. The substance may be an ointment, balm, salve and/or cream to aid the light treatment or to make the light treatment more pleasant. For example, the substance may be a cooling gel which keeps the skin temperature below 38 degrees. Alternatively, the substance may comprise a luminescent material for indicating which parts have already been treated with the light treatment system and for converting part of the light generated by the light treatment system to be visible through the window. Further alternatively, the substance may comprise a photo catalytic cleaning ointment which removes dead skin cells using, for example, deep blue light. Such removal of dead skin cells may improve the penetration depth of the light emitted by the light treatment system towards the part of the human or animal body.

BRIEF DESCRIPTION OF THE DRAWINGS

These and other aspects of the invention are apparent from and will be elucidated with reference to the embodiments described hereinafter.

In the drawings.

The figures are purely diagrammatic and not drawn to scale. Particularly for clarity, some dimensions are exaggerated strongly. Similar components in the figures are denoted by the same reference numerals as much as possible.

DETAILED DESCRIPTION OF EMBODIMENTS

Figure 1:
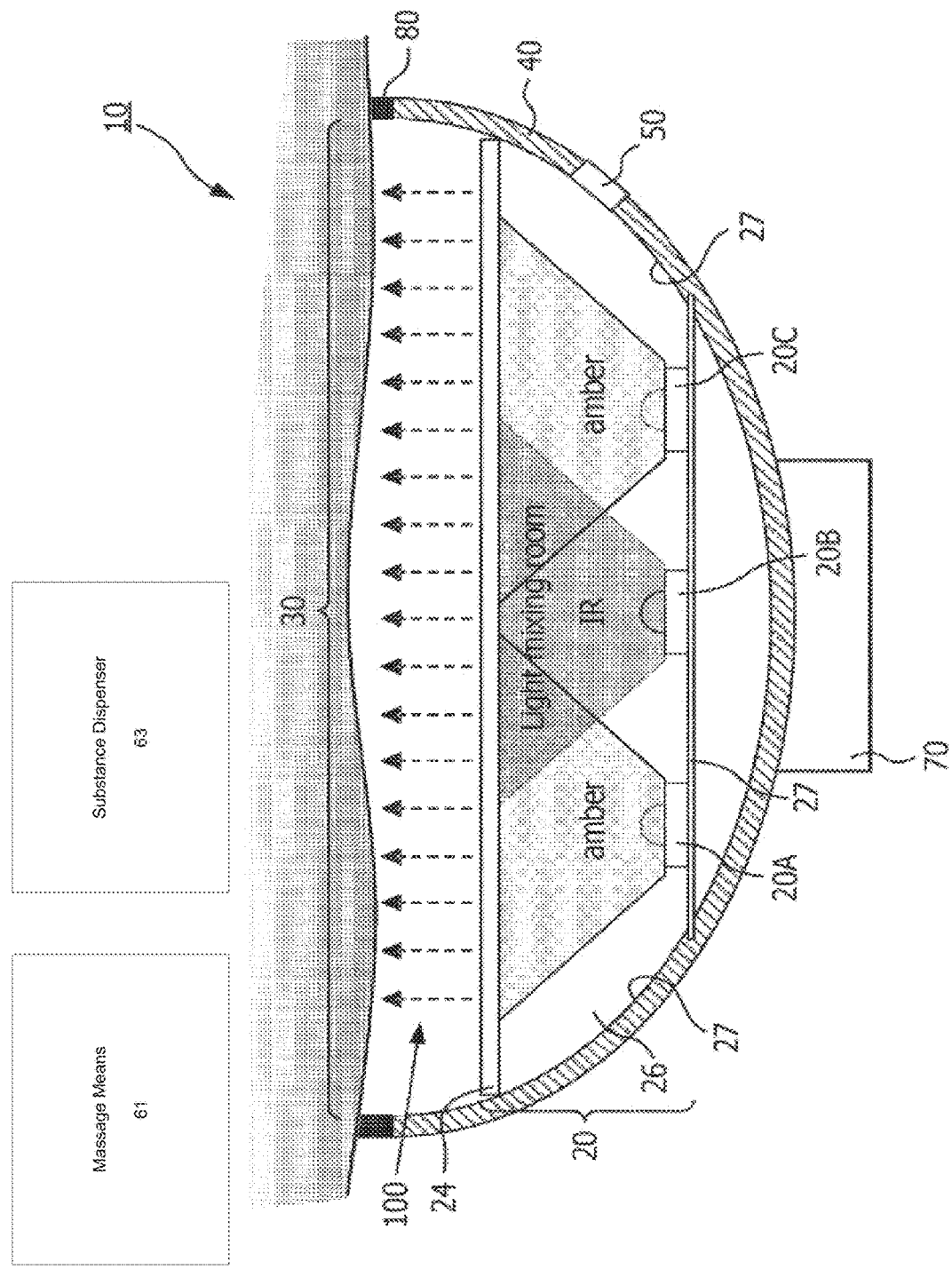
FIG. 1 shows a schematic cross-sectional view of a first embodiment of the light treatment system according to the invention.

FIG. 1 shows a schematic cross-sectional view of a first embodiment of the light treatment system 10 according to the invention. The light treatment system 10 comprises a housing 40 comprising a light source 20. In the embodiment shown in FIG. 1, the light source 20 comprises a plurality of light emitters 20A, 20B, 20C and, optionally, a light mixing chamber 26 for mixing the light emitted by the plurality of light emitters 20A, 20B, 20C. The inner wall of the housing 40 indicated with the arrows and reference number 27 preferably comprises a reflective surface for reflecting light towards the part of the human or animal body 30 which is to be treated in operation. Optionally, the light mixing chamber 26 may comprise a light emission window 24 which may be a diffusing window 24 for further mixing the light emitted from the light emission window 24 towards the part of the human or animal body 30 which is to be treated by the light treatments system 10. Alternatively, the light emission window 24 may not diffuse the light which is transmitted but may transmit the light substantially unhindered. In such a case the light emission window 24 may be configured for protecting the light emitters 20A, 20B, 20C from dirt and dust and/or from ointments, salves or creams which may be used during the light treatment.

In FIG. 1, the light emitted toward the part of the human or animal body 30 is indicated with dashed arrows 100 pointing towards the part of the human or animal body 30 which is to be treated by the light treatment system 10. The interface between the housing 40 and the part of the human or animal body 30 is provided with resilient material 80 which ensures a pleasant interface between the light treatment system 10 and the human or animal body. The resilient material 80 may also be used to ensure that no light leaks away from the housing 40 in an uncontrolled manner. Some of the light used for light treatment may be harmful. Such light may be damaging to the skin and/or eyes of the humans or animals undergoing the light treatment and/or to people assisting or providing the light treatment. As such, by using a resilient material 80 as interface between the housing 40 and the human or animal body, the leakage of light may be prevented.

In the housing 40 a window 50 is present for emitting light from an inner part of the housing 40 away from the housing 40. The window 50 in the housing 40 is used as an indicator 50 to indicate whether the light treatment system is operating and/or functioning well. As such, no additional light source and/or electronic circuitry is required for indicating whether the light treatment system is operating which typically reduces the overall power requirements of the light treatment system 10. A further benefit of the use of the window 50 is that the cost may be reduced as no additional light source and/or electronic circuitry is required. Because the light treatment system may be sold directly to consumers, an even marginal cost reduction is beneficial to the producer of the light treatment system.

The light treatment system 10 according to the invention may also comprise a control circuit 70 for controlling the light source 20. The control circuit 70 may, for example, control the light source 20 to emit the light towards the part of the human or animal body 30 in a pulsed mode operation. The time during which no light is emitted is indicated as dead-time. Most light treatment sequences require a pulsed mode of operation for the light treatment to be efficient. Because different treatment sequences may require a different frequency and/or a different dead-time, the light treatment system 10 according to the invention comprises the control circuit 70. The control circuit 70 may also be configured to control the different light emitters 20A, 20B, 20C of the light source 20. The controlling of the different light emitters 20A, 20B, 20C also include the situation in which the controller 70 operates the different light emitters 20A, 20B, 20C at different frequencies and at different dead-times. As such, different contributions of the light emitters 20A, 20B, 20C may be varied at will and/or as required to obtain an efficient light treatment.

A further benefit when being able to control the frequency and/or dead-time of the light source 20, and even to control the individual light emitters 20A, 20B, 20C is that a specific pulsed mode of operation may be selected such that the operation of the light source 20 in the light treatment system 10 may be perceived by the naked human eye as a substantially continuous illumination. Using, for example, a frequency above, for example, 50 Hertz, the flashing of the light source 20 is perceived as a substantial continuous light source 20 by the human eye. Because flashing light sources 20 may be perceived as annoying and may even cause health problems, the controlling of the frequency and/or dead-time to obtain an efficient light treatment while operating in a perceived continuous mode may be beneficial.

The light source may, for example, comprise a first light emitter 20A emitting amber light, a second light emitter 20B emitting infrared light and a third light emitter 20C emitting amber light. Such a configuration of light emitters 20A, 20B, 20C may beneficially be used for light treatment for skin rejuvenation. Alternatively other combinations of light emitters 20A, 20B, 20C may be used such that the light treatment system 10 may be used for the treatment of psoriasis, acne, vitiligo and skin cancer.

The light treatments system 10 according to the invention may also comprise massage means (not shown) for massaging the part of the human or animal body 30. Such massage means may improve the blood circulation and provide relaxation to the human or animal undergoing the treatment. The light treatment system 10 may also comprise dispensing means (not shown) for dispensing a substance to the part of the human or animal body 30. The substance may be an ointment, balm, salve and/or cream to aid the light treatment or to make the light treatment more pleasant. Such substance may be a cooling gel to keep the skin temperature below 38 degrees. The substance may also comprise a photo catalytic cleaning ointment which removes dead skin cells using, for example, deep blue light. Such removal of dead skin cells may improve the penetration depth of the light emitted by the light treatment system 10 towards the part of the human or animal body 30.

Figure 2:
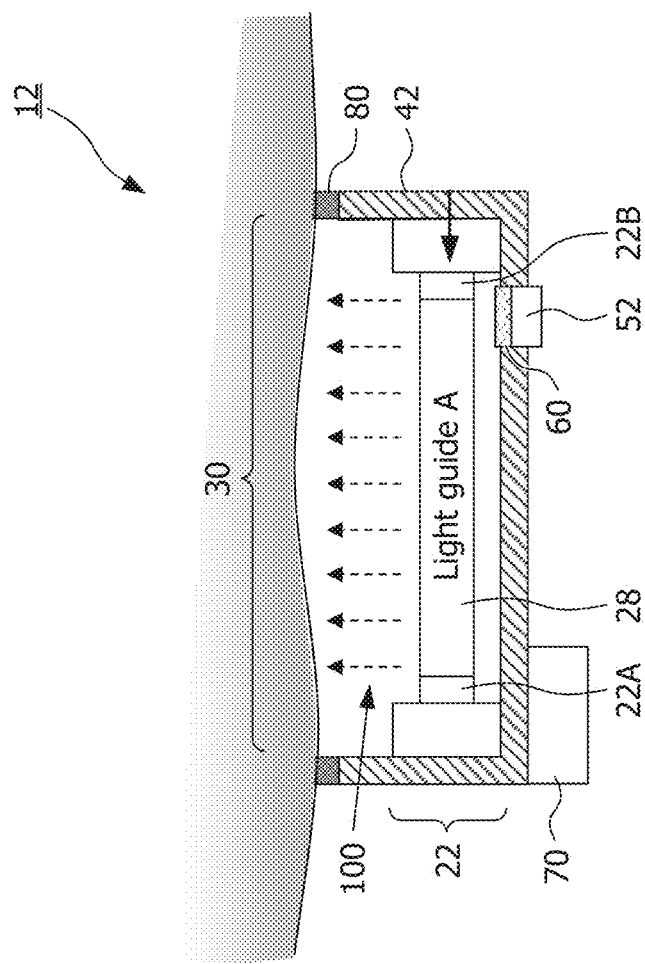
FIG. 2 shows a schematic cross-sectional view of a second embodiment of the light treatment system according to the invention.

FIG. 2 shows a schematic cross-sectional view of a second embodiment of the light treatment system 12 according to the invention. In the current embodiment the light source 22 is constituted of two light emitters 22A, 22B which emit light into a light guide 28. The light emitted by the light emitters 22A, 22B is mixed inside the light guide 28 before the light is emitted from the light guide 28 via light extraction means (not shown) toward the part of the human or animal body 30—again indicated with the dashed arrows having reference number 100. This second embodiment of the light treatments system 12 also comprises a housing 42 being connected to the human or animal body via the resilient material 80. Also a control circuit 70 is present for controlling the light source 22 and/or for controlling the individual light emitters 22A, 22B of the light source 22.

The embodiment of the light treatment system 12 as shown in FIG. 2 also comprises a window 52 for emitting light from an inner part of the housing 42 away from the housing 42. The window 52 as shown in FIG. 2 also comprises luminescent material 60 for converting at least a part of the impinging light from the light source 22 into light of a longer wavelength of which subsequently a part is transmitted through the window 52. The luminescent material 60 may be applied as a layer on a surface of the window 52. Alternatively, the luminescent material 60 may be mixed in the material of the window 52 (not shown) and as such, luminescent particles may be distributed throughout the window 52.

The luminescent material 60 of the window 52 may, for example, be configured for converting light impinging on the luminescent material 60 into light of a longer wavelength. When using the window 52 in the housing 42 as indicator to provide information about the working of the light treatment system 12, such indicator often is required to emit light of a specific color, for example, the color red. Choosing a specific luminescent material 60, part of the light emitted by the light source 20 may be converted into the right color to enable a red appearance of the window 52 when the light treatment system 12 is operating. Alternatively, the skin treatment may be done using light of a completely different color, for example, using substantially blue light or even light not visible to the human eye. A simple filtering of the light to only transmit the required component of the light may not work because the light used for the treatment may not comprise the required color component. In such a situation, a thin layer of luminescent material 60 on the window 52 or distributed inside the window 52 may be sufficient to convert light used for the light treatment on the part of the human or animal body 30 into light of a longer wavelength which may be visible and as such may be used as indicator for indicating whether the light treatment system 12 is working.

The luminescent material 60 may also be configured for absorbing ultraviolet light and for converting a part of the absorbed ultraviolet light into visible light. For some skin treatments, ultraviolet light is used. Such ultraviolet light may be harmful to the human eye and as such the housing 42 of the light treatment system 12 may be used to shield the harmful light from the human eye. Still, there should be a low-cost way to provide the user with information whether or not the light treatment system 12 is working properly. Using luminescent material 60 at or in the window 52 may convert some of the impinging ultraviolet light into visible light used to indicate the operation of the light treatment system 12.

In an alternative embodiment of the light treatment system 12 the luminescent material 60 comprises a decay time which is configured for reducing the dead-time of the light treatment system 10. This reducing of the dead-time may cause the light emitted at a specific frequency and having a specific dead-time to be perceived by the naked human eye as a substantial continuous light emission. The decay time of the luminescent material may, for example, be longer than the dead-time to generate a substantial continuous emission of light from the window. Alternatively, the decay time may be chosen such that the remaining dead-time is too short to be noticed by the naked human eye such that the emission from the window is perceived as being continuous by the naked human eye.

In an alternative embodiment, other light conversion means may be present inside the housing 52. In such an embodiment, the light conversion means may be part of the light treatment in which, for example, an ointment, salve or cream may be applied manually or via the dispensing means (not shown) to the part of the human or animal body 30, for example, to improve the absorption of the light emitted by the light treatment system 12 and/or the generate a light-enhanced or light-initiated chemical reaction which is required or beneficial for the light treatment therapy. Alternatively, the light conversion means 62 (see FIG. 3B) may be applied to a wall of the housing 42 of the light treatment system 12. Such an embodiment may be beneficial when using non-visible light for the light treatment of which a part of the non-visible light is converted by the light conversion means 62 into visible light of which a part is emitted via the window 56. Of course, applying the light conversion means 62 on the window 56 would result in a most efficient conversion requiring as little as possible light conversion means 62 as half of the light generated by the light conversion means 62 is emitted by the window 56.

Figure 3A:
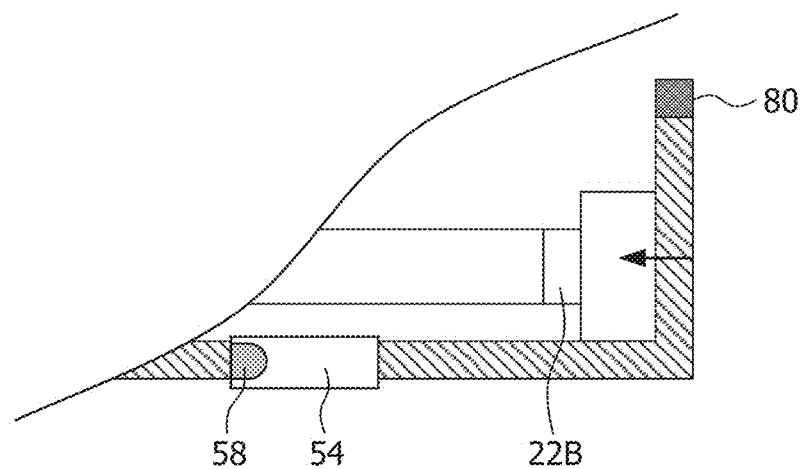
FIGS. 3A and 3B show schematic detailed sections of the second embodiment of the light treatment system having different windows.
Figure 3B:
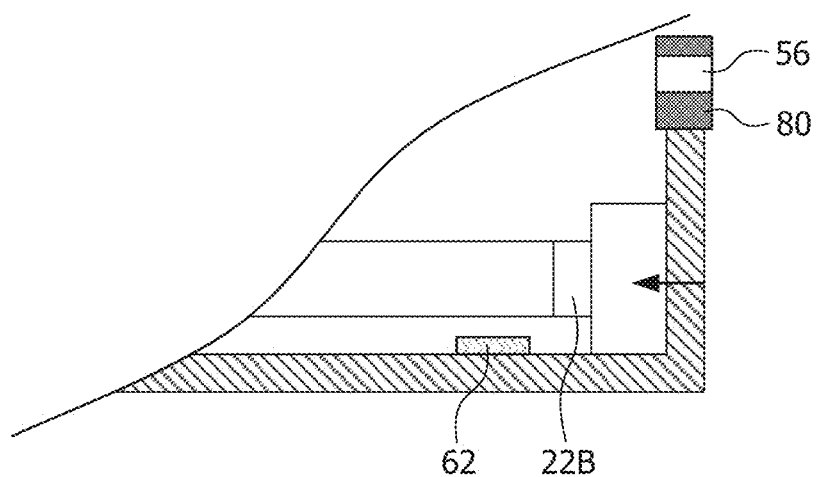

FIGS. 3A and 3B show schematic detailed sections of the second embodiment of the light treatment system 12 having different windows 54, 56. In the first detailed section, shown in FIG. 3A, the window 54 comprises a further light source 58 controlled by the control circuit 70. The further light source 58 may be controlled to emit light during at least a part of the dead-time. Such use of the further light source 58 provides similar beneficial effects in relation to the working conditions for the people operating the light treatment systems as mentioned above. Because the further light source 58 may be switched on during at least a part of the dead-time during which no light is emitted by the light treatment system 12 towards the part of the human or animal body 30, this additional light from the further light source 58 may cause the light emitted from the window 54 to be perceived as a substantial continuous emission of light.

In the embodiment shown in FIG. 3B the window 56 is arranged in the resilient material 80. Such an arrangement would allow a user to manipulate the dimensions of the window 56 by manipulating the amount of force with which the light treatment system 12 is applied to the human or animal body 30 and as such manipulate the amount of light transmitted through the window 56. In an alternative embodiment light conversion means 62 may be applied to the inner wall of the housing 42 of the light treatment system 12 for converting part of the light generated inside the light treatment system 12 into light of a different wavelength which may be visible through the window 56.

It should be noted that the above-mentioned embodiments illustrate rather than limit the invention, and that those skilled in the art will be able to design many alternative embodiments without departing from the scope of the appended claims.

In the claims, any reference signs placed between parentheses shall not be construed as limiting the claim. Use of the verb "comprise" and its conjugations does not exclude the presence of elements or steps other than those stated in a claim. The article "a" or "an" preceding an element does not exclude the presence of a plurality of such elements. The invention may be implemented by means of hardware comprising several distinct elements. In the device claim enumerating several means, several of these means may be embodied by one and the same item of hardware. The mere fact that certain measures are recited in mutually different dependent claims does not indicate that a combination of these measures cannot be used to advantage.

The invention claimed is:

1. A light treatment system comprising:
    an ultraviolet treatment light source configured to emit an ultraviolet treatment light of a treatment wavelength directed towards a part of a human or animal body for light treatment, configured to directly irradiate said part of said human or animal body,
    a housing configured to cover the treatment light source from exterior view and configured to at least partially cover the illuminated part of the human or animal body from external view,
    an indication window of the housing configured to allow the emission of an indication light of an indication wavelength from an inner part of the housing away from the housing in a direction different from the direction towards the part of the human or animal body of the treatment light,
    wherein the indication light emitted by the indication window is sourced from the treatment light source and comprises transformed light of a different wavelength than the treatment wavelength of the treatment light emitted by the light source directed towards the part of the human or animal body for treatment thereof.

2. The system of claim 1, wherein the difference between the indication wavelength and the treatment wavelength comprises the indication wavelength is longer than the treatment wavelength.

3. The system of claim 1, comprising a light converter within the housing, configured to convert at least a part of the treatment light of the treatment wavelength impinging on the light converter into the transformed indication light of the different indication wavelength.

4. The system of claim 3, wherein the light converter comprising luminescent material within the indication window, the luminescent material converting the treatment light impinging on the luminescent material into indication light of a longer wavelength.

5. The system of claim 4, wherein the light converter is configured to absorb ultraviolet light and to convert a part of the absorbed ultraviolet light into visible light.

6. The system of claim 1, comprising a control circuit configured to control the treatment light source to emit the treatment light towards the part of the human or animal body in a pulsed mode operation comprising a dead-time during which no treatment light is emitted by the treatment light source towards the part of the human or animal body.

7. The system of claim 6, wherein the control circuit is configured to control a frequency and/or dead-time of the pulsed mode operation, the frequency and/or dead-time being selected to be perceived by a naked human eye as a substantially continuous illumination of the part of the human or animal body while still providing an effective light treatment.

8. The system of claim 6, wherein the window comprises a further light source controlled by the control circuit for emitting light during at least a part of the dead-time during which no treatment light is emitted by the treatment light source towards the part of the human or animal body.

9. The system of claim 6 comprising a light converter comprising luminescent material within the indication window, the luminescent material converting the treatment light impinging on the luminescent material into indication light of a longer wavelength, the luminescent material being pre-selected to have a sufficient decay time so that the dead time of the Treatment light emission resulting in dead-time of the indication light emission from the window is perceived by the naked human eye as a continuous light emission.

10. The system of claim 1, wherein the housing comprises resilient material for contacting the human or animal body and preventing light from leaking between the housing and the human or animal body.

11. The system of claim 10, wherein the window for indication light emission is arranged in the resilient material.

12. The system of claim 1, wherein the treatment light source comprises a first light emitter and a second light emitter, the first light emitter emitting light comprising a different spectrum from the spectrum of light emitted from the second light emitter.

13. The system of claim 12 comprising a control circuit for controlling the treatment light source for emitting the light towards the part of the human or animal body in a pulsed mode operation, wherein the control circuit is configured for controlling the first light emitter to emit light at a first pulsed mode of operation and for controlling the second light emitter to emit light at a second pulsed mode of operation being different from the first pulsed mode of operation.

14. The system of claim 12, wherein:
the first light emitter emits ultraviolet light and the second light emitter emits visible light, or
the first light emitter emits ultraviolet light and the second light emitter emits infrared light, or
the first light emitter emits visible light and the second light emitter emits infrared light, or
the first light emitter emits ultraviolet light comprising light of a first wavelength and the second light emitter emits ultraviolet light comprising light of a second wavelength, or
the first light emitter emits visible light and the second light emitter emits visible light.

15. The system of claim 1, comprising:
a massager to message the part of the human or animal body covered by the housing.

16. The system of claim 1, comprising:
a substance dispenser to dispense a substance onto the part of the human or animal body covered by the housing.

17. A method of operating a light treatment system, comprising:
covering a part of a human or animal body with a housing to at least partially prevent external view of the covered part of the human or animal part;
emitting ultraviolet treatment light from an ultraviolet treatment light source covered by the housing, the ultraviolet treatment light source having a treatment wavelength and being directed towards the part of a human or animal body covered by the housing, to provide a light treatment to the part of the human or animal,
irradiating said part of said human body or animal body with the ultraviolet treatment light emitted from the ultraviolet treatment light source,
emitting an indication light sourced from the emitting treatment light via an inner part of the housing and passing from the inner part of the housing through an indication window in the housing, the indication light having an indication wavelength and being in a direction different from the direction towards the part of the human or animal body of the treatment light,
wherein the indication light emitted by the indication window comprises essentially light of a different wavelength than the treatment wavelength of the treatment light emitted by the light source directed towards the part of the human or animal body for treatment thereof.

18. A control circuit that is not a transitory propagating signal or wave, the circuit comprising control information for controlling a method of operating a light treatment system, comprising:
covering a part of a human or animal body with a housing to at least partially prevent external view of the covered part of the human or animal part;
emitting treatment light from an ultraviolet treatment light source covered by the housing, the ultraviolet treatment light source having a treatment wavelength and being directed towards the part of a human or animal body covered by the housing, to provide a light treatment to the part of the human or animal,
irradiating said part of said human body or animal body with the treatment light emitted from the ultraviolet treatment light source,
emitting an indication light sourced from the emitting treatment light via an inner part of the housing and passing from the inner part of the housing through an indication window in the housing, the indication light having an indication wavelength and being in a direction different from the direction towards the part of the human or animal body of the treatment light,
wherein the indication light emitted by the indication window comprises essentially light of a different wavelength than the treatment wavelength of the treatment light emitted by the light source directed towards the part of the human or animal body for treatment thereof.

* * * * *